United States Patent [19]

Altobelli et al.

[11] Patent Number: 5,683,406

[45] Date of Patent: Nov. 4, 1997

[54] APPARATUS AND METHOD FOR HARVESTING BONE

[75] Inventors: David E. Altobelli; Peter R. Ebner, both of Hollis, N.H.

[73] Assignee: Maxilon Laboratories, LLC, Hollis, N.H.

[21] Appl. No.: 537,303

[22] Filed: Sep. 29, 1995

[51] Int. Cl.$^6$ .................................................. A61B 17/32
[52] U.S. Cl. .......................... 606/170; 606/167; 604/22; 30/317
[58] Field of Search ..................... 606/80, 167, 170, 606/171, 176, 177, 178, 84, 79, 131, 160, 161, 132, 133; 128/754, 752, 758, 757; 604/22; 30/317, 136

[56] References Cited

U.S. PATENT DOCUMENTS

| | | | |
|---|---|---|---|
| 2,526,662 | 10/1950 | Hipps et al. | |
| 2,876,777 | 7/1959 | Kees, Jr. | 606/84 |
| 3,661,144 | 5/1972 | Jensen et al. | 128/758 |
| 3,889,657 | 6/1975 | Baumgarten | 128/758 |
| 4,043,322 | 8/1977 | Robinson | 128/758 |
| 4,221,222 | 9/1980 | Detsch | |
| 4,366,822 | 1/1983 | Altshuler | 128/753 |
| 4,466,429 | 8/1984 | Loscher et al. | |
| 4,686,972 | 8/1987 | Kurland | |
| 4,722,338 | 2/1988 | Wright et al. | |
| 4,798,213 | 1/1989 | Doppelt | 128/754 |
| 4,844,064 | 7/1989 | Thimsen et al. | |
| 4,932,957 | 6/1990 | Zwick | 128/758 |
| 4,994,024 | 2/1991 | Falk | 604/22 |
| 5,052,411 | 10/1991 | Schoolman | 128/863 |
| 5,133,359 | 7/1992 | Kedem | 128/754 |
| 5,250,065 | 10/1993 | Clement et al. | 128/758 |
| 5,269,785 | 12/1993 | Bonutti | 606/80 |
| 5,403,317 | 4/1995 | Bonutti | 606/80 |

OTHER PUBLICATIONS

Neo–Contemporary Co., Inc.; "Two Perfect Instruments For Every Rhinoplastic Surgeon –The Rubin Sterile Disposable Cartilage Planer"; 1986; Neo–Contemporary Co., Inc.
Goldman et al; "Periodontal Therapy"; 1980; pp. 991–1007; The C.V. Mosby Company, St. Louis.
Hutchinson; "Osseous Coagulim Collection Filter"; 1973; pp. 688–689, 690; J. Periodontology.
Haggerty et al; "Autogenous Bone Grafts: A Revolution in the Treatment of Vertical Bone Defects"; 1971; pp. 626–627, 629, 637, 641; J. Periodontology.
Robinson; "Osseous Coagulum for Bone Induction"; 1969; pp. 5–12; J. Peridontology.

*Primary Examiner*—Michael Buiz
*Assistant Examiner*—Patrick W. Rasche
*Attorney, Agent, or Firm*—Hayes, Soloway, Hennessey, Grossman & Hage, P.C.

[57] ABSTRACT

An instrument for harvesting bone comprises an elongate body having a hollow, and a proximal end and a distal end communicating with one another through the hollow. A blade having a cutting edge for cutting or abrading bone is mounted adjacent an aperture in the distal end. The cut or abraded bone moves through the aperture and into the hollow.

23 Claims, 11 Drawing Sheets

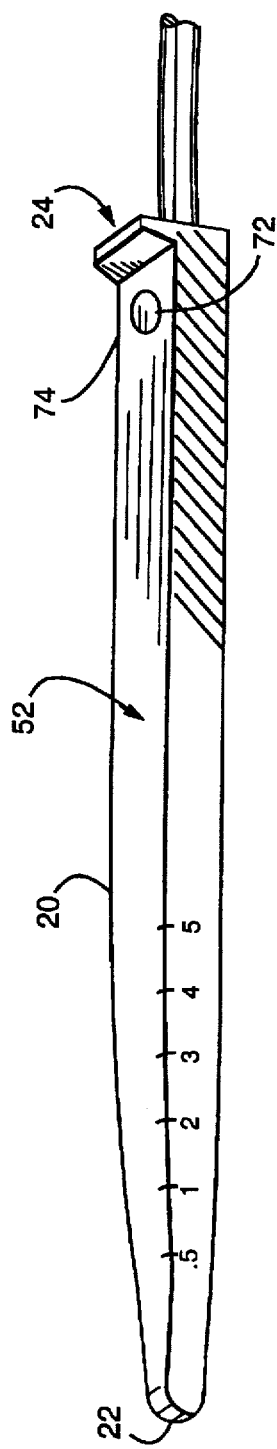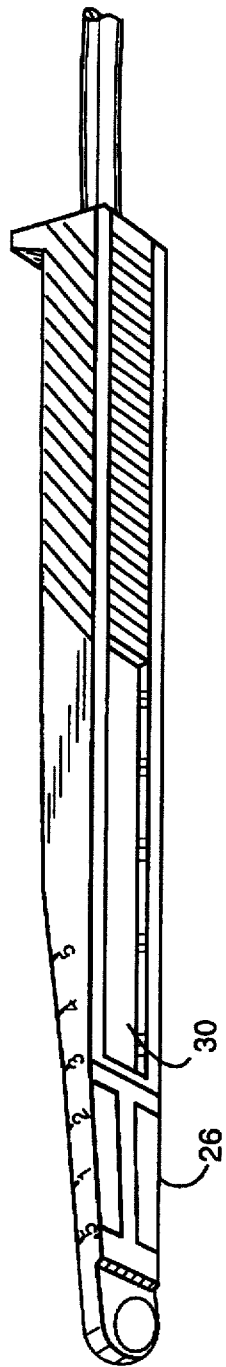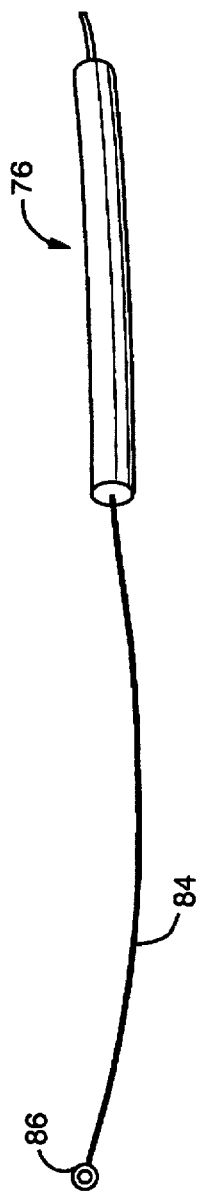

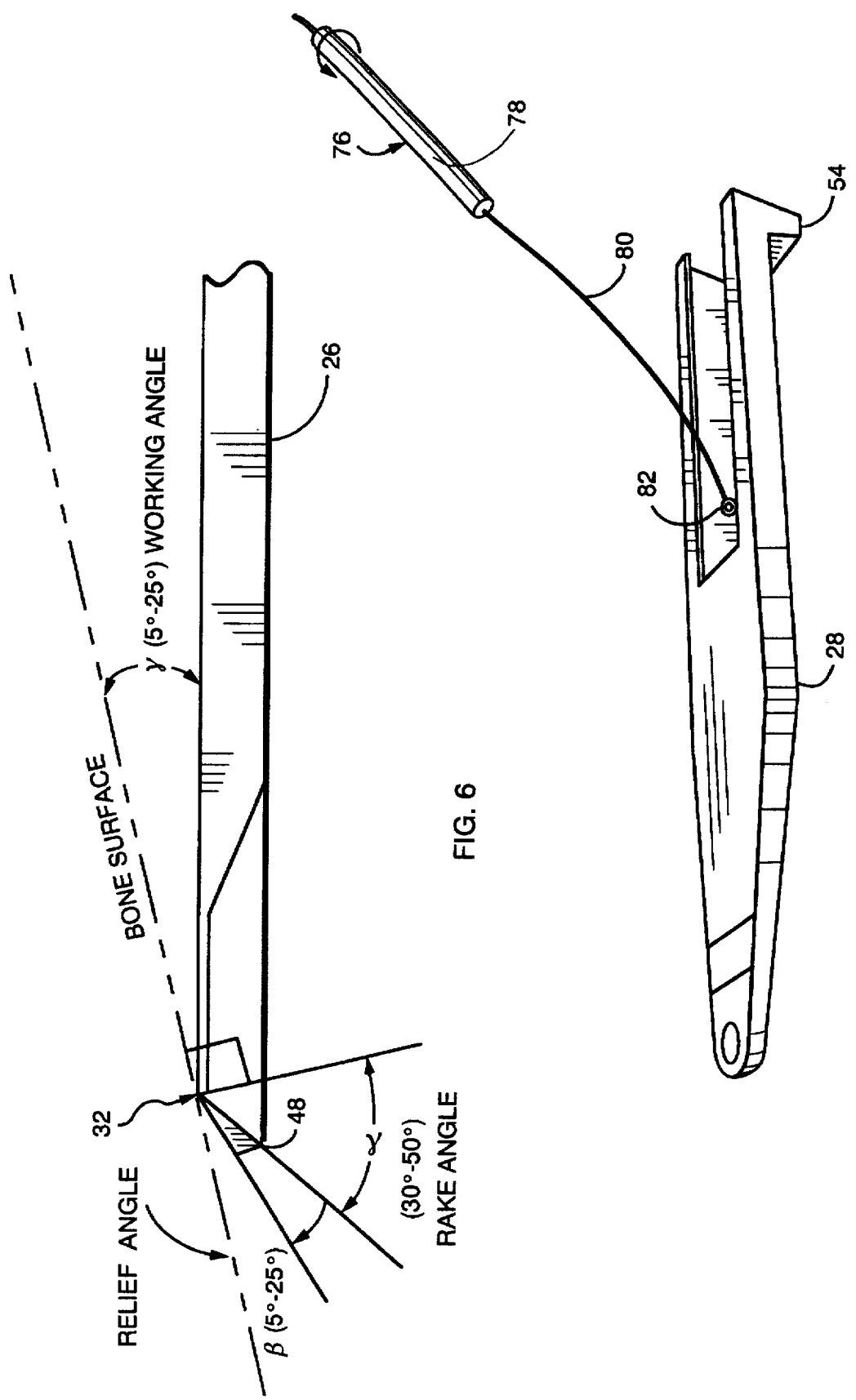

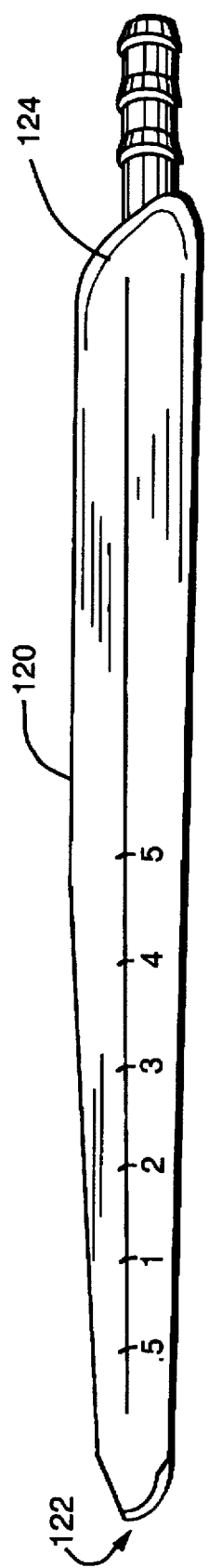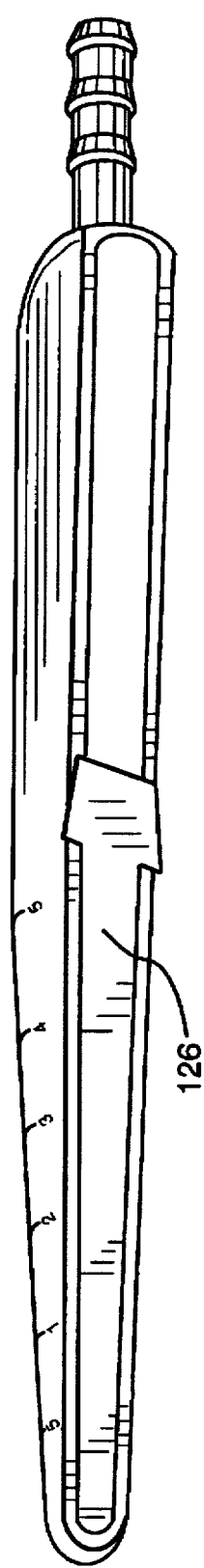
FIG. 11
FIG. 12

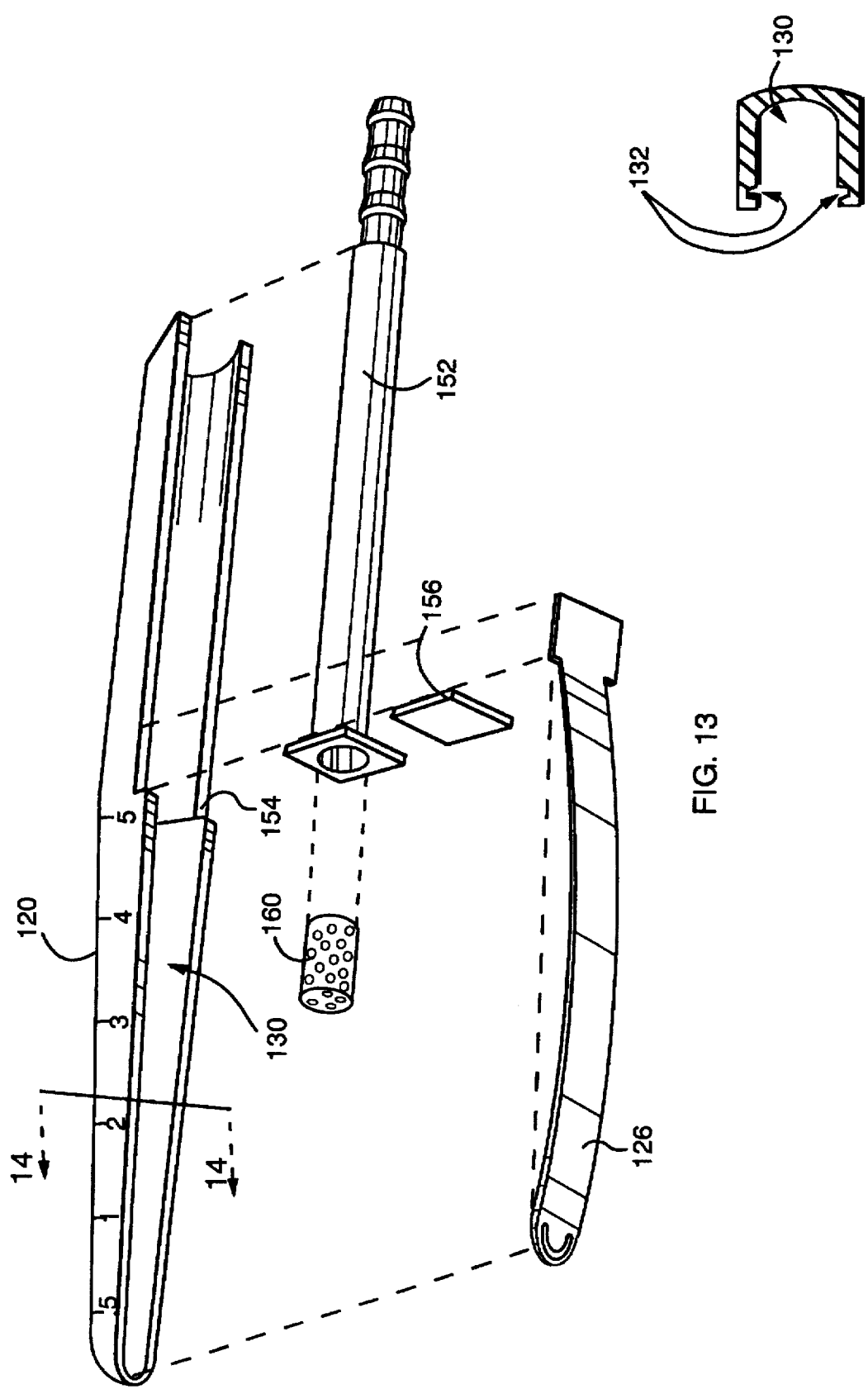

APPARATUS AND METHOD FOR HARVESTING BONE

BACKGROUND OF THE INVENTION

1. Technical Field

The present invention relates to the field of surgery. The invention has particular utility in connection with the removal and collection of bone from one or more donor sites, and the preparation and placement of the bone material at a second location in the patient, e.g. for use in bone grafting peridontal defects or dental implants, surgery, although other utilities are contemplated.

2. Description of Prior Art

Many reconstructive procedures used in medicine and dentistry involve the manipulation and healing of bones. Such procedures may involve changes in the position, orientation, shape and size of skeletal structures. A problem that is commonly encountered during such procedures is a lack of bone graft material. Bone graft material may be used in several applications, such as to fill between sections of bone that have been repositioned, to change surface geometry, or to add bone to an area that is deficient, such as in conjunction with periodontal surgery or dental implants in the patients' jaws.

The need to harvest small bone grafts from intraoral sites has been common in periodontal surgery to restore bone defects around teeth. In the case of dental implant surgery, bone grafts may be needed to augment atrophic alveolar ridges of the maxilla and/or mandible and the sinus floor to increase the dimension of these bone sites to accommodate and totally cover the endosseous portion of implant fixtures. Bone grafts also are used in conjunction with guided tissue regeneration, a technique that uses a membrane to isolate hard tissue from soft tissue sites and potentiate hard tissue healing.

Presently, it is often difficult to harvest adequate amounts of autogenous bone from intraoral sites. Therefore, clinicans often rely on non-autogenous sources of graft material, such as bone from cadaver sources (homologous or allogenic grafts), animal sources (heterogenous or xenogeneic grafts), or synthetic bone substitutes. However, healing of non-autogenous material grafts is not as extensive or predictable as healing of autogeneous bone obtained directly from the patient; plus there is the additional cost of such non-autogenous graft materials which can be significant.

Clinicians use several techniques to remove bone for grafting for intraoral procedures. In one such technique rotary instruments, such as side cutting burrs or trephines, are used to remove a piece or section of cortical bone from a local intraoral site in the maxilla or mandible. The cortical bone is often morsalized into a particulate form, either manually with a rongeur like instrument or in a bone mill. The particulate bone is then combined with blood to form an osseous coagulum, and then is curretted and packed into the osseous defect around the teeth or implant. See Robinson, R. E. "Osseous Coagulum for Bone Induction", J. Periodontology 40:503(1969). Suction devices with filters have been fabricated and manufactured to collect the bone dust from rotary instruments. See Hutchinson, R. A. "Utilization. of an Osseous Coagulum Collection Filter", J. Periodontology 44:668(1973). See also Goldman, et al, "Periodontal Therapy", pp 994–1005, C. V. Mosby Co., (1980); and Haggarty, et al., "Autogeneous Bone Grafts: A Revolution in the Treatment of Vertical Bone Defects", J. Periodontology 42:626 (1971). While such techniques are widely used by clinicians, the techniques have limitations, since sites to harvest sections of intraoral bone are limited in number and extent because of limited intraoral access, proximity to tooth roots, nerve structures and sinus cavities, and thin plates of bone.

Other techniques for harvesting bone include using chisels or osteotomes to remove and manually collect shavings from the surface. These instruments must be very sharp and the process is often awkward and time consuming. Another technique is to collect bone dust generated by twist drills or taps used to prepare the sites for implant placement. However, much of the bone material may be lost while the site is being irrigated to cool the cutting instrument. When larger amounts of bone are needed for major reconstructive procedures, other sites such as the hip (anterior or posterior ilium), tibia, ribs, or the calvarium often are used. However, using such other sites necessitates a second surgical site, which may require post-operative hospitalization, and thus is less amenable, e.g. in the case of an out-patient dental procedure.

Various surgical devices have been proposed and/or are in use to harvest bone marrow samples for biopsy or devices such as rongeurs or bone cutters or punches to remove sections or convex edges of bone. Surgical devices also are in use in arthroscopy and endoscopy for cutting or drilling bone or tissue and removing the tissue fragments. Ultrasonic devices to cut bone also are in use; however, such devices require the removal of the irrigant and debris liberated by the apparatus. Each of these methods and/or devices, however, suffers from one or more deficiencies as applied to the collection of bone for grafting.

Yet other patented devices have been proposed; each of these, however, suffers from one or more deficiencies:

U.S. Pat. Nos. 5,403,317 and 5,269,785 to Bonutti show a method and apparatus for the percutaneous cutting and removal of tissue fragments from human. The Bonutti device removes the tissue fragments by suction, where it can be collected and then placed elsewhere in the patient from where originally obtained. Bonutti employs a flexible drill, and suction to remove the debris to an externally placed collection reservoir, where it is compressed before being replaced into the patient.

U.S. Pat. No. 2,526,662 to Hipps discloses a bone meal extractor apparatus for mechanically removing bone meal from a donor bone site through a small percutaneous site using a drill, The drill shavings, which comprise primarily sub-surface bone, are then evacuated into an open cut that the drill passes through, for collection.

U.S. Pat. No. 4,798,213 to Doppelt teaches a device for obtaining a bone biopsy for diagnosis of various bone diseases. The Doppelt device is intended to remove a core of bone using a tubular drill, while maintaining the architecture of the tissue. The sample is obtained from the marrow space and not intended from re-implantation.

U.S. Pat. No. 5,133,359 to Kedem shows a hard tissue biopsy instrument in which samples are taken using a rotatably driven hollow needle.

U.S. Pat. No. 4,366,822 to Altshuler discloses a method and apparatus for bone marrow cell separation and analysis. The Altshuler apparatus collects bone marrow cells in a filtration chamber on a filter interposed between a needle directed into the bone marrow site and an aspirator or vacuum source, i.e. using negative pressure to withdrawal marrow cells through a needle.

U.S. Pat. No. 5,052,411 to Schoolman teaches a vacuum barrier attachment for shielding the operator of a medical tool from harmful aerosols and blood, etc. created by drilling, sawing types of actions, etc. The Schoolman device requires vacuum and is not intended for harvesting tissue for re-implantation.

U.S. Pat. No. 4,722,338 to Wright et al discloses a device instrument for removing bone which uses a shearing action similar to a rongeur to cut bone, with means for collecting fragments of bone as they are removed. The Wright et al device reportedly is used mainly for the removal of projections or edges of bone using a shearing mechanism without the intent of harvesting the bone for grafting.

U.S. Pat. No. 4,994,024 to Falk teaches an arthroscopy hook-clippers device that allow the unobstructed removal of tissue or bone with removal of the fragments by suction. The Falk device is intended for arthroscopy applications and with the removal of projections of tissue or bone and not specifically for the harvest of tissue for grafting.

Yet other prior art devices are disclosed in U.S. Pat. No. 4,466,429 to Loscher et al and U.S. Pat. No. 4,844,064 to Thimsen et al.

It is thus a primary object of the present invention to provide an improved method and device for removing and harvesting bone or the like, and delivering the bone to a second site, which overcomes the aforesaid and other disadvantages of the prior art. A more specific object of the present invention is to provide an improved method and device for directly, percutaneously or permucosally removing and collecting bone from one or more donor sites, and for temporarily storing the collected bone and preparing the bone for delivery to a preselected recipient site.

SUMMARY OF THE INVENTION

According to the present invention there is provided a surgical instrument for removing bone for grafting procedures, and comprising an elongate hollow body having a proximal end and a distal end communicating with one another through said hollow. A scraping knife or blade is located adjacent the distal end, and includes a cutting edge for cutting or abrading bone into the hollow by way of a valved or greatly narrowed passageway. Additionally, the instrument preferably includes means for affixing the proximal end of the instrument to a vacuum source. Completing the instrument, in one preferred embodiment, are means for mixing the harvested bone material with a binder, and a plunger for expelling the collected bone material through an orifice in the distal end of the instrument, to a delivery site. In another preferred embodiment of the invention, the instrument includes means for disposing the blade between a first position in which the blade is exposed for scraping and collecting bone material, and a second position in which the cutting edge of the blade is shielded.

BRIEF DESCRIPTION OF THE DRAWINGS

Still other features and advantages of the present invention will become apparent from the following detailed description of the invention, taken in conjunction with the accompanying drawings wherein like numerals depict like parts, and wherein:

FIG. 1 is a perspective view showing the top and side of an instrument made in accordance with one preferred embodiment of the present invention;

FIG. 2 is a perspective view showing the bottom and side of the instrument of FIG. 1;

FIG. 3 is a perspective view showing details of the mixing impeller employed in connection with the instrument of FIG. 1;

FIG. 6 is a cross-sectional view showing details of the blade of the instrument of FIG. 1;

FIG. 7 is a perspective view from the bottom of the instrument of FIG. 1, with the slide portion removed, and the mixing device impeller introduced therein;

FIG. 11 is a view similar to FIG. 1, and showing an alternative embodiment instrument made in accordance with the present invention;

FIG. 12 is a view, similar to FIG. 2, and showing the bottom and side of the instrument of FIG. 11;

FIG. 13 is an exploded view of the instrument shown in FIG. 12;

FIG. 14 is a cross-sectional view taken along section 14—14 of FIG. 13;

DETAILED DESCRIPTION OF A PREFERRED EMBODIMENT

Figure 4:
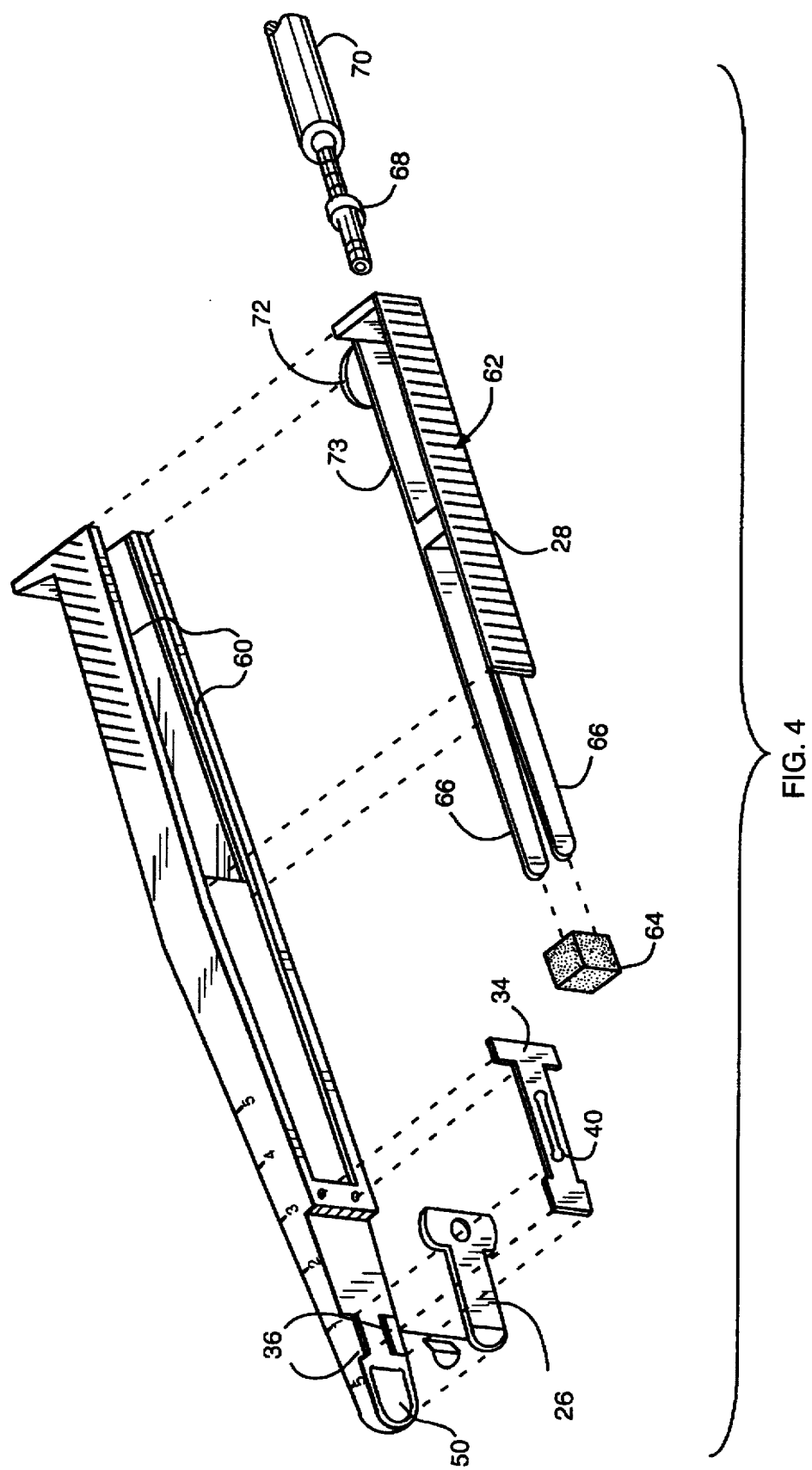
FIG. 4 is an exploded view taken from the perspective of FIG. 2.

Referring to FIGS. 1–7 of the drawings in which there is illustrated a preferred embodiment of surgical instrument made in accordance with the present invention. The surgical instrument comprises an elongate housing 20 which is sized and shaped to fit comfortably and securely in the hand of the user. Housing 20 comprises an elongate rigid body comprising a distal end 22 and a proximal end 24. Housing 20 is a formed of a surgical grade material which preferably is transparent at least in part, and serves to support a scraping blade 26 as will be described in detail hereinafter, and a slidably mounted plunger mechanism 28 which also will be described in detail hereinafter. Housing 20 includes a hollow which defines a storage chamber or reservoir 30 for holding bone fragments separated by blade 26, or collected by vacuum as will be described in detail hereinafter. Chamber 30 also serves as a mixing chamber in which, for example, a binder, blood or other graft materials, growth factors, cultured cells, antibiotics, or other biologic or non-biologic materials, may be added to the bone fragments collected therein for delivery, with the bone fragments, to a desired site.

Figure 5:
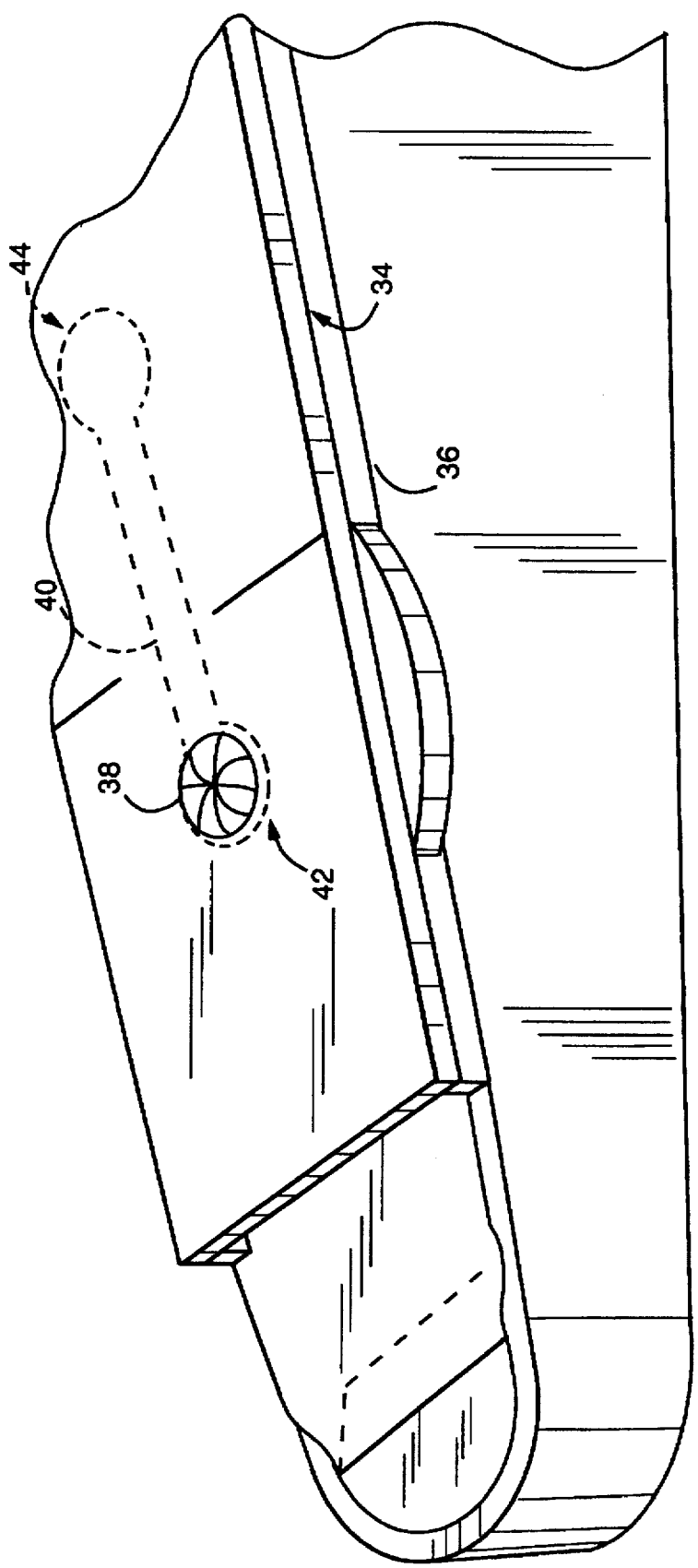
FIG. 5 is an enlarged perspective view showing details of the distal end of the instrument of FIG. 1, taken from the bottom view.

Referring in particular to FIGS. 4–6, blade 26 is mounted at the distal end 22 of housing 20 and is slidably mounted between an open position in which the blade cutting edge 32 is operatively disposed adjacent the distal end 22 of housing 20, and a closed position (shown in phantom in FIG. 5) in which the cutting edge 32 of the blade is positioned below a cover member 34. Blade 26 is slidably mounted in tracks 36 formed in housing 20, and is held in place by cover 34. Blade 26 is selectively locked in an operative position (i.e. open) and a stowed position (i.e. closed) by a detent 38 formed on the surface of the blade, which slides in track 40 on cover 34 between an operative position 42 and stowed position 44. Integrally formed blade grips 46 extend outwardly under cover 34, so as to facilitate the users sliding the blade between the operative and stowed positions.

Referring also to FIG. 6, blade 26 comprises a sharpened loop 48 having a rake angle m preferably in the range of 30°–50°, and a relief angle β preferably in the range of 5°–25°. The distal end 22 of housing 20 is tapered in width and height to provide the user with as unobstructed view of the bone scraping/collection site as possible, and to provide easier access to constricted surgical sites. An elliptical aperture 50 formed in the underside of the distal end 22 of housing 20 provides an inlet for cuttings or shavings liberated by the blade to enter chamber 30. Aperture 50 also allows the contents of chamber 30 to be expelled at the time of delivery as will be described in detail hereinafter.

Housing 20 preferably is flat on its upper surface 52 so as to provide a comfortable place for the user to rest an index finger and to apply controlled downward pressure during collection of bone. A small projection 54 adjacent the proximal end of housing 20 on its upper side provides a stop for the hand of the user when gripping the instrument. Also, when the instrument is turned over and the plunger removed, e.g. to allow additives to be introduced into the chamber 30, the protrusion sits on the table and tips the instrument such that additives like liquids or particulate substances tend to passively descend and flow into chamber 30. The aperture 50 at the distal end of the instrument also allows various adapters to be secured to the end of the instrument, such as various shaped delivery tips and adapters and cowlings, as well as a sealing plug.

The instrument also includes a plunger mechanism 28 which is designed so that it can be easily advanced with the thumb of the user while the instrument is held in a delicate fashion such as one might hold a pencil. Plunger mechanism 28 is slidably mounted in housing 20 in a pair of parallel slide tracks 60 formed in the side walls of the housing. The bottom surface 62 of slide 28 has surface contour to allow it to be easily gripped and moved by the thumb of the user.

A foam block 64 is carried at the distal end of the plunger for wiping the sides of the reservoir 30, and for advancing substances in the reservoir to the distal end of the instrument, where the material may then be expelled through aperture 50, and delivered to a selected site. In a preferred embodiment of the invention, the plunger mechanism 28 comprises a pair of flexible fingers 66 for supporting foam block 64. Foam block 64 preferably is of an open cell, surgical grade foam as to allow the passage of air and fluids, but not particulate substances.

The plunger mechanism 28 also includes a fitting 68 for attachment of tubing 70 to the proximal end of the instrument, so that suction or positive pressure may be applied to the instrument, as desired. Also tubing 70 permits the introduction of various fluids or gases into the instrument. A detent button 72 on the proximal end of a plunger mechanism 28 allows the plunger mechanism to be locked in place when pressure or suction is being applied to the instrument. Detent button 72 is mounted adjacent the distal end of a cantilevered arm 73 of plunger mechanism 28, where it may engage an opening 74 in the proximal end of the instrument's upper side. In use, detent button 72 is manually depressed to release the plunger so that the plunger may be advanced. In a preferred embodiment of the invention, fitting 68 is snap-fitted into the proximal end of the instrument, and interferes with the plunger release detent button 72, so that the button 72 cannot be depressed downward into the chamber.

Referring in particular to FIGS. 3 and 7, a mixing impeller 76 which may be used to combine substances with harvested bone and/or declog the instrument tip is included in a preferred embodiment of the invention. Mixing impeller 76 comprises a short cylindrical handle 78 to one end of which is mounted a stiff, slightly curved wire 80 having a loop 82 at its tip, so that when the mixing impeller 76 is rotated along its long axis or moved in a reciprocating manner, it will agitate and combine substances in chamber 30. At the other end of the handle 78 is fitted a stiff wire 84 having a ball tip 86 that can be introduced into the instrument aperture 50 to clear debris from this site.

Figure 17:
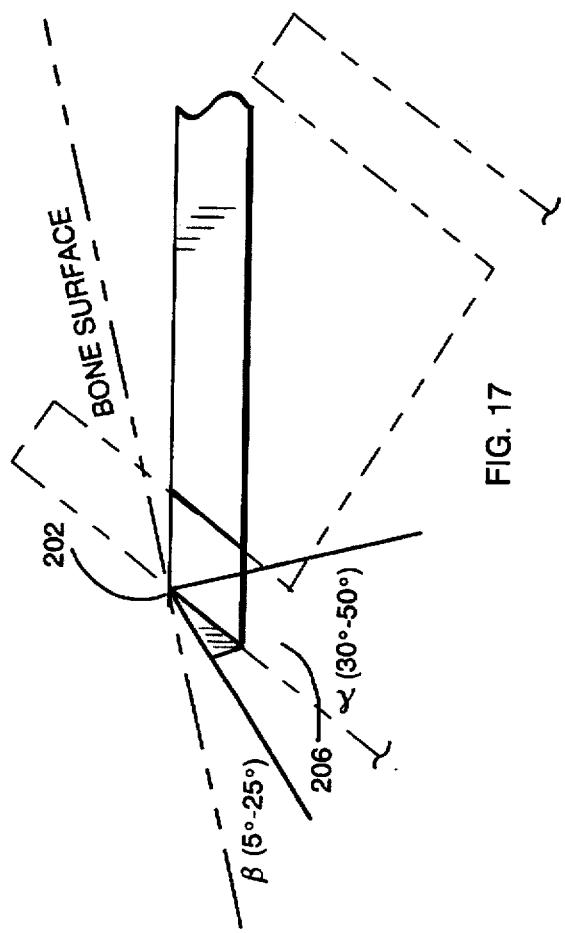
FIG. 17 is a side elevational view, in cross-section, taken along the mid-section of the blade element shown in FIG. 16.
Figure 18:
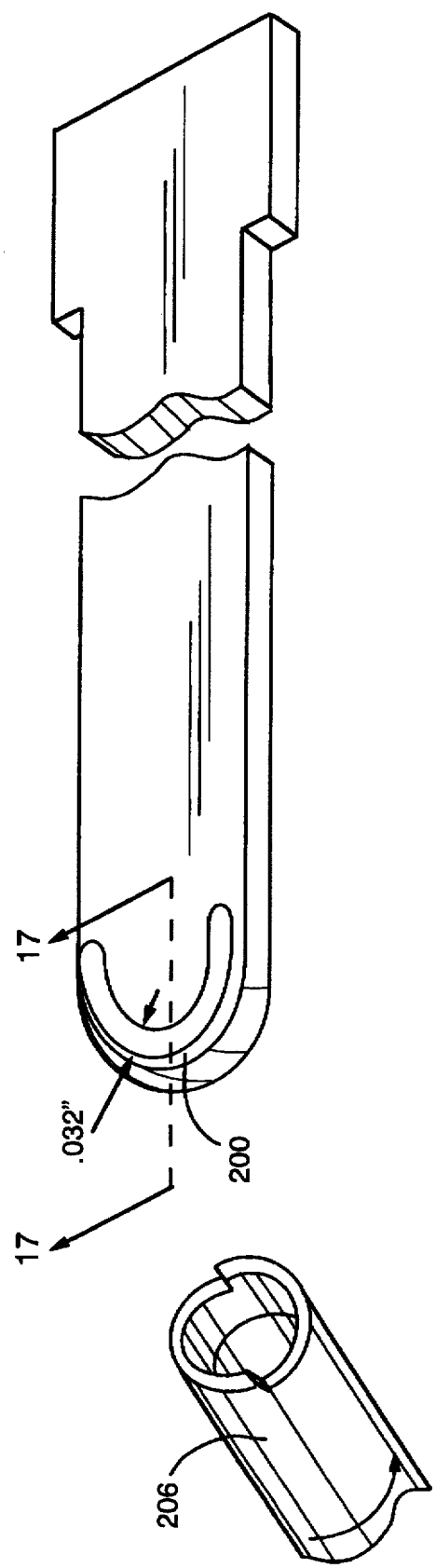
FIG. 18 is a side elevational view, in cross-section, showing the cutting blade at an intermediate stage in the production thereof.
Figure 19:
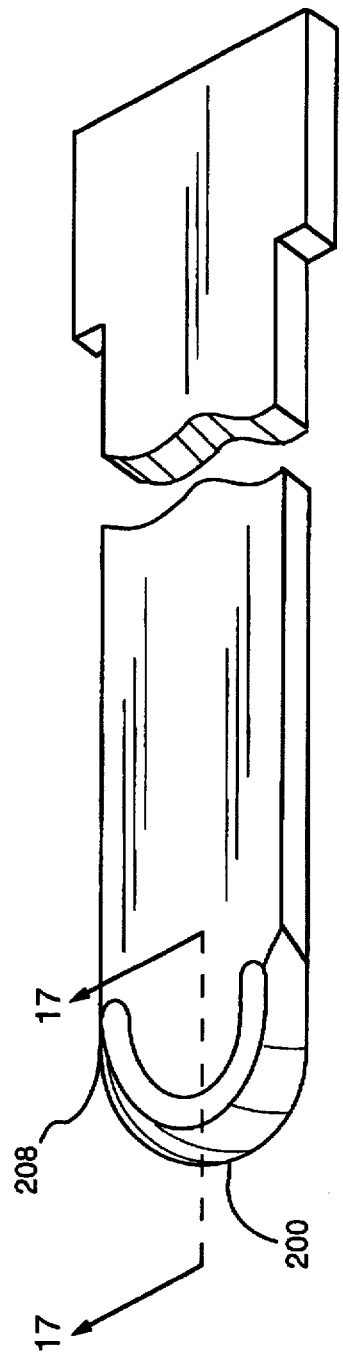
FIG. 19 is a view, similar to FIG. 18, and showing the cutting blade after further processing.

Referring also to FIG. 19, blade 126 preferably is made of a hardened stainless steel, and is predominantly flat or may be slightly bowed longitudinally, with the blade distal end 90 rounded and the proximal end somewhat rectangular 92. Referring also to FIGS. 17–18, the cutting edge of blade 126 preferably is formed as a sharpened contoured loop 200 by first milling a semicircular angular slot 202 in a piece of flat stock stainless steel using an angled hollow core milling tool or drill bit (shown in phantom at FIG. 17 at 206). Loop 200 is then ground at an angle using a grinding wheel or the like so as to produce a sharpened loop having a cutting edge 208.

If desired, the cutting surface 94 of the blade can be treated with a TiN coating or the like to preserve its hardness. As noted supra, blade 126 is carried in a track that allows it to be positioned and locked in a forward or cutting position, and retracted in a non-cutting position so that the contents of the chamber may be expelled or delivered through aperture 50. In the retracted position, the cutting edge 94 of the blade is safely covered by blade cover 34. Blade 126 also can be locked in an intermediate position, e.g. to secure various adapters in aperture 50.

The cutting edge of blade 126 has a positive rake angle; and the blade is designed to have a functional range of inclination to provide flexible operation when accessing various skeletal sites. Preferably, the leading edge of the blade has at least a 10° relief. A flexible metal flap 100 (FIG. 5) is attached to the blade 126 in a preferred embodiment of the invention. Flap 100 allows passage of bone shavings past the cutting edge of the blade and into the collection chamber, while maintaining the collected bone fragments within the chamber.

Preferably, the cutting edge of the blade is curved, with the apparent convexity of the blade preferably greater with increased inclination of the handle. This allows the blade tip to access narrow concavities in bone(s). When the handle is more parallel to the bone surface, the apparent convexity of the blade is less, and a more broad area of bone is removed. This format is intended for flat or convex surfaces.

In a preferred embodiment of the invention, blade 26 can be removed from the handle when it is brought to its most fully retracted position and rotated laterally so that substitute blades, e.g. with various shaped cutting edges can be used with the instrument.

A particular feature and advantage of the present invention is that it permits removal and harvesting a thin layer of surface bone from almost any bone surface. This increases the number of possible donor sites and minimizes structural or contour compromise to the donor site while providing the clinician with significant amounts of autogenous bone graft material. Another feature and advantage of the present invention is that the harvested bone is in a particulate or a bulked fibrous like state which increases its apparent volume and facilitates its placement in the recipient sites and optimizes bone cell survival.

Figure 9:
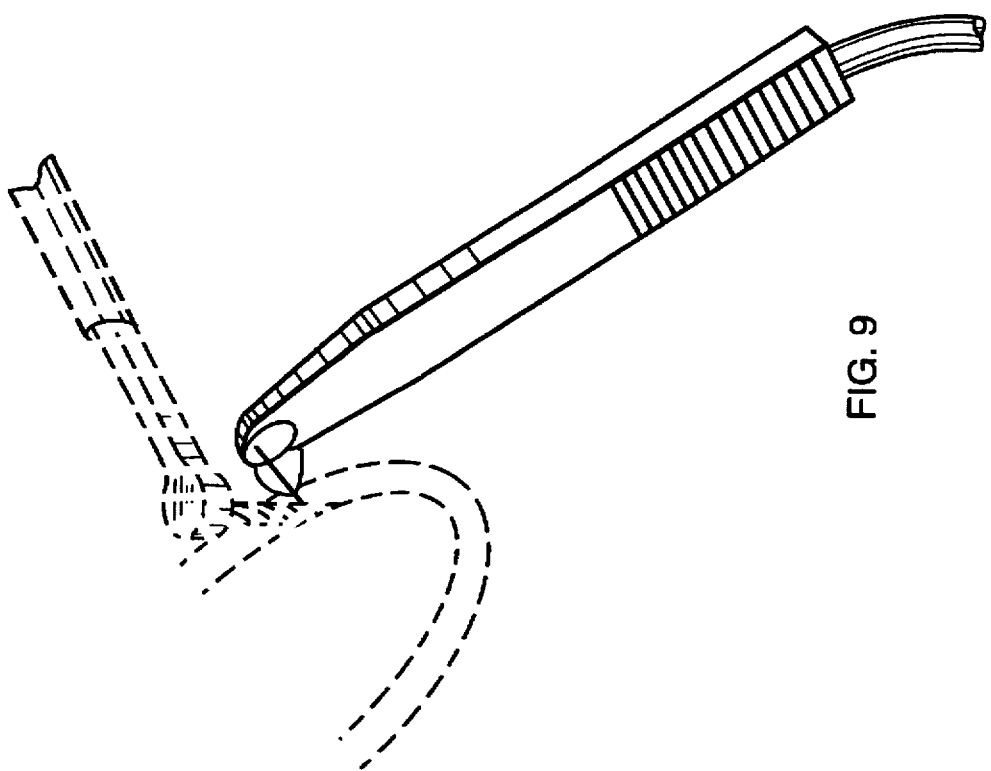
FIG. 9 is a view similar to FIG. 8, and showing the use of the surgical instrument of FIG. 1 in collecting bone fragments and finds created by drilling the bone of a patient.
Figure 8:
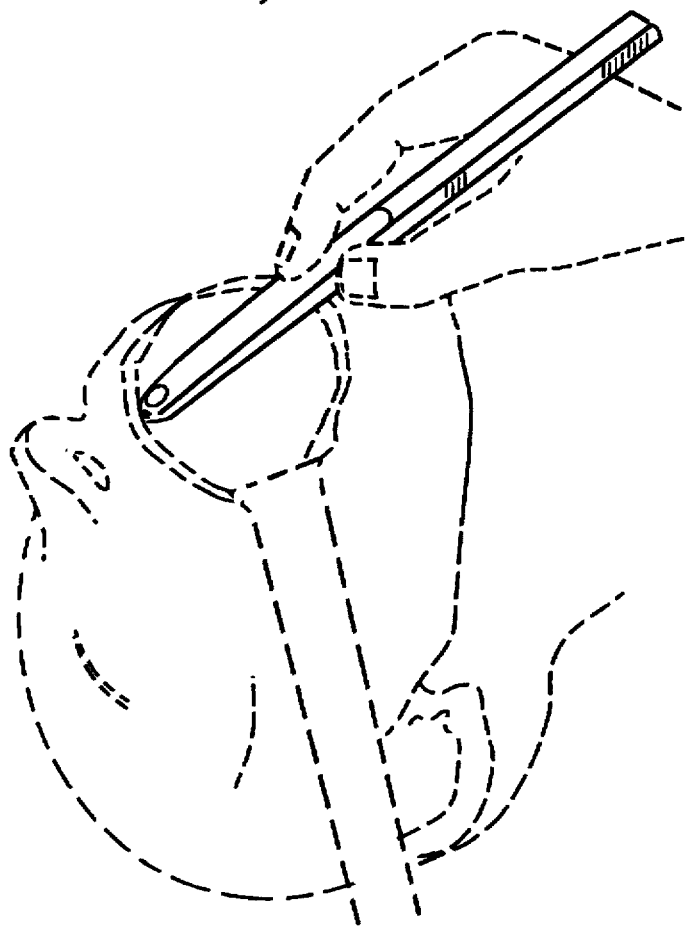
FIG. 8 is a perspective view showing the use of the surgical instrument of FIG. 1 to collect bone from an intraoral site on a patient.
Figure 10:
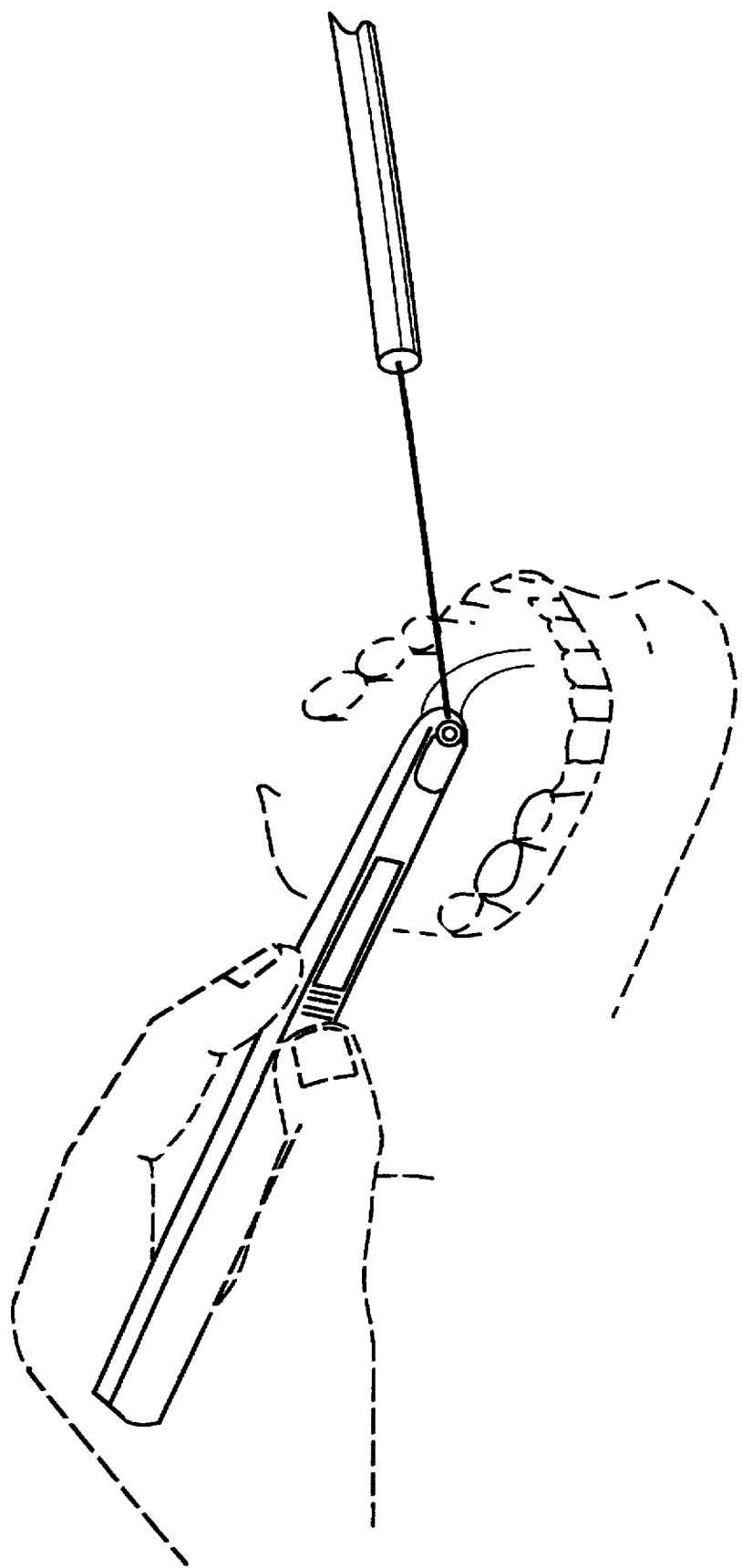
FIG. 10 is a view similar to FIG. 8, and showing the use of the instrument to dispense bone mix to a recipient site on a patient.

Various changes may be made in the above invention without departing from the spirit and scope thereof. For example, as shown in FIG. 9, the instrument of the present invention advantageously may be used as collecting instrument for vacuum collection of particulate bone produced, e.g. by a drill. The particulate bone may then be mixed with a binder or blood or the like in chamber 30 and delivered to a desired site through aperture 50.

Figure 15:
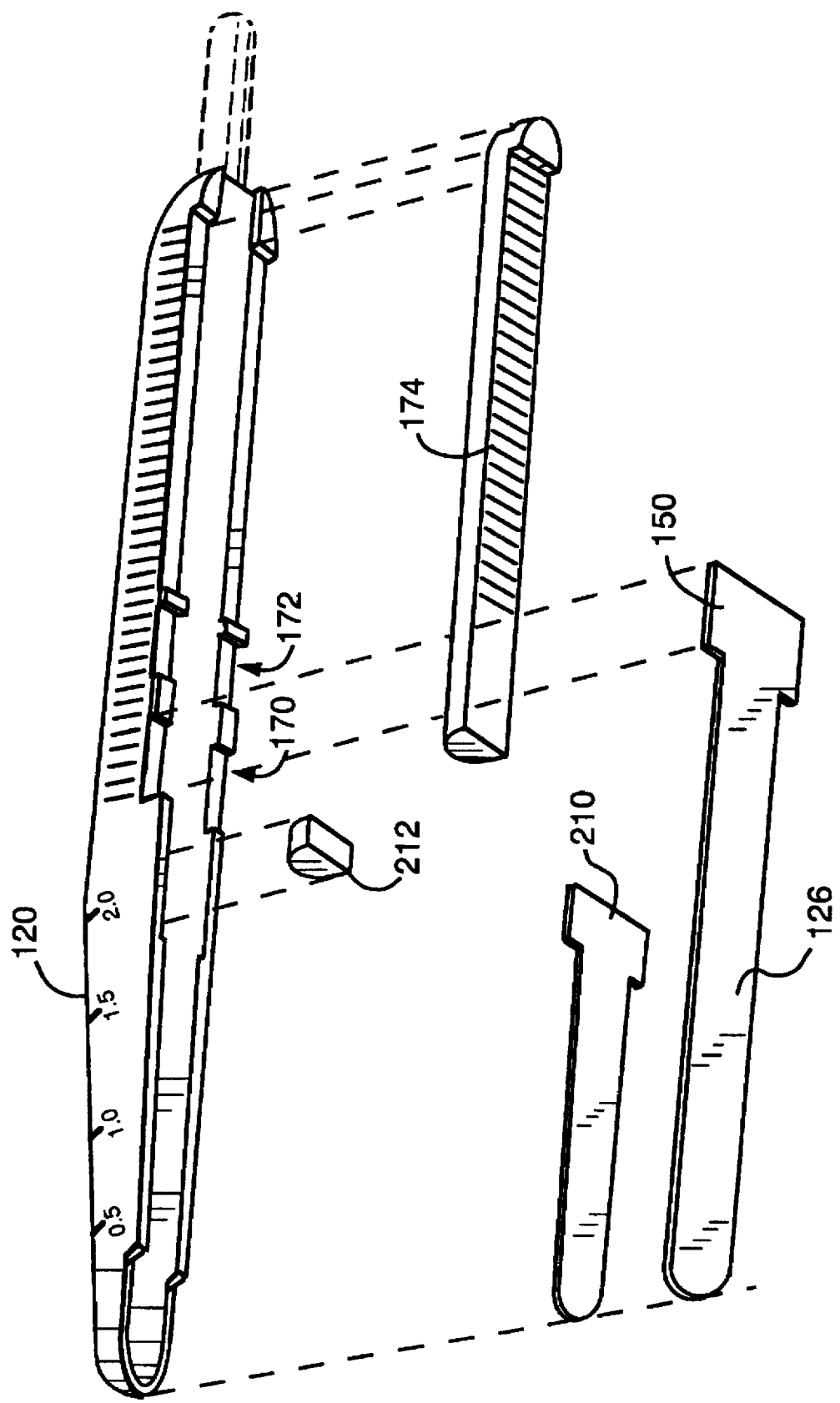
FIG. 15 is a view similar to FIG. 13, and showing yet another embodiment of instrument made in accordance with the present invention.
Figure 16:
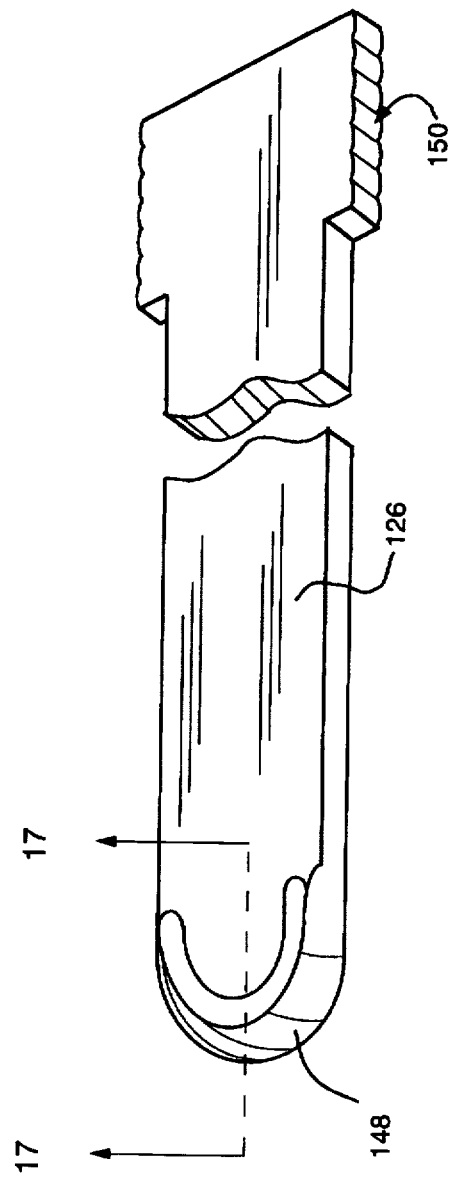
FIG. 16 is an enlarged perspective view showing details of the cutting blade element in accordance with the preferred embodiment of the invention.

Referring to FIGS. 11–14, there is illustrated another embodiment of surgical instrument in accordance with the present invention. In this embodiment, the surgical instrument comprises an elongate housing 120 which is sized and shaped to fit comfortably and securely in the hand of the user. Housing 120 comprises an elongate rigid body comprising a distal end 122 and a proximal end 124. Housing 120 is formed of surgical grade stainless steel, or a surgical grade plastic or ceramic, and serves to support a scraping blade 126 as will be described in detail hereinafter. Housing 120 includes a hollow which defines a storage chamber or reservoir 130 for holding bone fragments separated by blade 126, or collected by vacuum as will be described in detail hereinafter. Referring in particular to FIGS. 15 and 16, blade 126 is slidably mounted in grooves 132 formed in the inner walls of the distal end of body 120. Preferably, although not necessarily, as shown in FIG. 13, blade 126 is slightly bowed longitudinally so that when the blade is inserted in grooves 132, the blade is held in place therein, i.e. by friction fit. Referring also to FIG. 16 and 17, blade 126 is similar to blade 26 (FIGS. 5 and 6) and includes a sharpened loop 148 at its distal end having a rake angle œ in the range of 10–50 degrees, preferably about 20–40 degrees, and a relief angle β in the rate of 5–25 degrees, preferably about 10 degrees. A pair of integral wings or grips 150 are formed adjacent the proximal end of blade 126 for facilitating handling the blade, and for removing the blade from body 120 and replacement with a fresh blade.

Referring again to FIG. 13, a vacuum hose adaptor 152 is slidably mounted in grooves 154 formed mid-point of body 120, and also serves to retain blade 126 in position in the body. Alternatively, a blank (shown in phantom at 156) may be inserted in grooves 154 to hold blade 126 in position. A porous filter plug 160, e.g. formed of a foam block or the like is mounted adjacent the distal end of adapter 152. Filter 160 preferably is formed of an open cell, surgical grade foam so as to allow the passage of air and fluids, but not particulate bone substances.

In yet another embodiment of the invention, as shown in FIG. 15, body 120 includes two detent positions, 170, 172, for accommodating blade wings 150 so that blade 126 may be affixedly positioned between a collecting position 170, and a retracted position 172 where the bone particulates may be dispensed. Completing the FIG. 15 embodiment is a slide member 174 which may be friction fitted in body 120.

Still other changes may be made in the invention. For example, as shown in phantom at FIG. 15, a vacuum hose barb may be molded to the proximal end of body 120. Also, while the invention in preferred embodiment has been illustrated comprising a handle comprising a one-piece member having a hollow for collecting harvested bone, the handle may include a removable cartridge for collecting harvested bone. Also, if desired, a closure means 210 may be slidably mounted under blade 126 (see FIG. 15). In such case, additional detent positions (not shown) should be provided in the side walls of body 120 for accommodating the closure blade wings so that closure blade 210 may be fixedly positioned between a retracted position and a sealing position. Yet other changes are possible. For example, one or more fractionable pouches 212 for containing a binder, growth factors, antibiotics or other biologic or non-biologic materials may be preloaded in body 120, fractionable by plunger 174 so that such materials may be then admixed with the harvested bone.

It will thus be appreciated that there has been described an improved apparatus and method for harvesting bone which achieves the foregoing and other objects.

What is claimed is:

1. An instrument for harvesting bone, comprising an elongate body having distal and proximal ends, said body having a hollow interior for holding harvested bone, an aperture communicating with said interior, a loop shaped blade mounted in the distal end of said body, said blade having a cutting edge for cutting and abrading bone, a concave proximal surface of said cutting edge defining one side of an elongated slot restricting said aperture, another side of said elogated slot being defined by a distal end of a convex surface, having a bone engaging bottom surface extending across said blade and limiting penetration by said cutting edge into the bone surface, the distal end of said convex surface being proximally spaced from the cutting edge defining said slot, the proximal surface of said cutting edge serving to direct cut bone across said slot onto an upper surface of said convex surface through said aperture and into said hollow interior.

2. An instrument according to claim 1, and including a removable slide mounted adjacent the proximal end of said instrument.

3. An instrument according to claim 2, wherein said slide comprises a plunger assembly.

4. An instrument according to claim 3, wherein the collected bone can be consolidated in the hollow interior with the plunger.

5. An instrument according to claim 3, wherein the collected bone can be pushed out of the hollow interior through the handle aperture with the plunger.

6. An instrument according to claim 2, and further comprising means for fixedly positioning said slide in a locked position.

7. An instrument according to claim 2, wherein said slide is removable whereby to provide access to said hollow.

8. An instrument according to claim 1 and including means adjacent said proximal end for connecting said instrument to an optional vacuum source.

9. An instrument according to claim 1, wherein said blade is moveably mounted between an operative position and a protected position.

10. An instrument according to claim 1, wherein said blade comprises a curved cutting edge.

11. An instrument according to claim 1, wherein said blade is bowed longitudinally.

12. An instrument according to claim 1, wherein the cutting edge of said blade is hardened.

13. An instrument according to claim 1, wherein said slot retains said cut bone in said hollow.

14. An instrument according to claim 1, wherein said hollow comprises a removable cartridge carried on said body.

15. An instrument according to claim 1, and further comprising a fractionable pouch carried within said hollow.

16. The instrument according to claim 1, wherein the convex loop is mounted for movement with respect to said aperture so as to effectively enlarge said slot.

17. The instrument according to claim 16, wherein the convex surface is part of the blade and the blade is moved with respect to the aperture.

18. The instrument according to claim 16, wherein the convex surface is separate from the blade and the convex surface is moved towards the proximal end of said blade to increase the size of said slot.

19. The instrument according to claim 1, wherein the cutting edge and the distal end of the convex surface are generally parallel.

20. The instrument according to claim 1, wherein said slot is substantially uniform from side to side across the instrument.

21. An instrument according to claim 1, wherein said cutting edge of said blade is coated with a hardened material.

22. An instrument according to claim 1, wherein said slot retains said abraded bone in said hollow.

23. A blade for harvesting bone, said blade having a body with distal and proximal ends, said blade being loop shaped at its distal end, said loop being sharpened to an edge for cutting and abrading bone, a concave proximal surface of said loop shaped blade defining one side of an elongated slot, another side of said slot being defined by a convex distal portion proximally spaced from the cutting edge having a bone engaging bottom surface across said blade and limiting penetration by said cutting edge into the bone, the proximal surface of the loop serving to direct cut bone across said slot and onto an upper surface of said convex distal portion.

* * * * *